United States Patent
Wan et al.

(10) Patent No.: US 10,390,803 B2
(45) Date of Patent: Aug. 27, 2019

(54) FECES SAMPLING AND DETECTING DEVICE AND METHOD FOR DETECTING FECES BASED ON THE DEVICE

(71) Applicant: W.H.P.M. BIORESEARCH AND TECHNOLOGY CO., LTD., Beijing (CN)

(72) Inventors: John Wan, Beijing (CN); Chunhua Yuan, Beijing (CN); Qinghai Xia, Beijing (CN)

(73) Assignee: W.H.P.M. BIORESEARCH AND TECHNOLOGY CO., LTD., Beijing (CN)

( * ) Notice: Subject to any disclaimer, the term of this patent is extended or adjusted under 35 U.S.C. 154(b) by 597 days.

(21) Appl. No.: 14/779,685

(22) PCT Filed: Feb. 28, 2014

(86) PCT No.: PCT/CN2014/072716
§ 371 (c)(1),
(2) Date: Sep. 24, 2015

(87) PCT Pub. No.: WO2014/154079
PCT Pub. Date: Oct. 2, 2014

(65) Prior Publication Data
US 2016/0051235 A1 Feb. 25, 2016

(30) Foreign Application Priority Data

Mar. 25, 2013 (CN) .......................... 2013 1 0097892

(51) Int. Cl.
| A61B 10/00 | (2006.01) |
| G01N 21/77 | (2006.01) |
| G01N 21/78 | (2006.01) |

(52) U.S. Cl.
CPC ......... *A61B 10/0038* (2013.01); *G01N 21/78* (2013.01); *G01N 2021/7759* (2013.01)

(58) Field of Classification Search
CPC ............... A61B 10/0038; G01N 21/78; G01N 2021/7759
See application file for complete search history.

(56) References Cited

U.S. PATENT DOCUMENTS

2006/0210448 A1* 9/2006 Wang ................. A61B 10/0038
422/400
2008/0034899 A1* 2/2008 Kikuiri .............. A61B 10/0038
73/864.51

(Continued)

OTHER PUBLICATIONS

Examination Report No. 1 for standard patent application issued in Australian Application No. 2014243587 dated Apr. 18, 2017.

(Continued)

*Primary Examiner* — Robert J Eom
(74) *Attorney, Agent, or Firm* — Scully, Scott, Murphy & Presser, P.C.

(57) ABSTRACT

The present invention provides a feces sampling and detecting device and a method for detecting feces based on the feces sampling and detecting device. The device includes a detector, a casse with detecting strips provided in the detector, a collector accommodated in the detector detachably, a feces sampler for sealing the collector detachably, and at least one puncturing part arranged at a bottom of the detector facing one side of the collector. The feces sampling and detecting device can detect collected feces quickly, thereby avoiding feces sample from nature changing in an interval period, and preventing liquid in the collector from entering the detector to influence safety of the device of the present invention.

20 Claims, 8 Drawing Sheets

(56) References Cited

U.S. PATENT DOCUMENTS

2008/0286831 A1 11/2008 Liang
2009/0024055 A1 1/2009 Nguyen et al.

OTHER PUBLICATIONS

Supplementary European Search Report dated Oct. 12, 2016 issued in Application No. EP 14 77 5040.

* cited by examiner

FECES SAMPLING AND DETECTING DEVICE AND METHOD FOR DETECTING FECES BASED ON THE DEVICE

TECHNICAL FIELD OF THE INVENTION

The present invention relates to feces sampling and detecting device and a method for detecting feces based on the device of the present invention, which belongs to the field of medical apparatus and medical detection.

BACKGROUND OF THE INVENTION

Feces detection is usually applied to early screening of many diseases, for example, it can be screened whether a patient suffers from gastrointestinal bleeding by testing haemoglobin in feces. So feces detection becomes a routine item for detecting diseases in many medical units.

In the existing process of feces detection, feces is first collected in a feces sampling device by a patient, and then the feces in the feces sampling device is placed in a special feces detecting device for detecting by a medical staff. Operating like this disables the patients to detect the feces by themselves. In addition, because the collecting device and the detecting device are two separate apparatus, a sample in the feces collecting device cannot be detected immediately, after a period of time, the nature of feces usually changes, which causes an inaccurate detection result. In addition, when the operation is finished, the medical staff needs to abandon the feces collecting device and the detecting device separately, and so many collecting devices and detecting devices occupy a lot of space.

A feces sampling and occult blood self testing device is disclosed in a Chinese patent 201210299951.4; this self testing device is composed of a cover, a main body container, a feces sampling rod guiding channel in the main body container, a feces dissolving tank at lower part in the main body container, a feces liquid filtering tube below the feces dissolving tank, a communicating tube and detecting strips detection accommodating slot on the side wall of the main body container. The cover is fixed with or not fixed with a feces sampling rod; the top of the feces sampling rod is fixed at the internal top wall of the cover; the feces sampling rod is inserted in the feces sampling rod guiding channel, and the bottom of the feces liquid filtering tube is connected with the bottom of the detecting strips detection accommodating slot through the communicating tube. The device has both the feces sampling function and the feces detecting function. However, in the process of manufacturing the device, because the internal structure of the main body container is complex, it is very difficult to mould; in addition, because of a special position of the feces dissolving tank, it is very difficult for a sealing membrane to seal. In addition, because the top of the feces dissolving tank is sealed by the sealing membrane, once the sealing has problem, liquid in the whole dissolving tank will moisten the detecting strips in the detecting strips detection accommodating slot, which influences the detection.

Therefore, a device which has both the feces sampling function and the feces detecting function and is highly safe and easy to be moulded is needed.

SUMMARY OF THE INVENTION

A purpose of the present invention is to provide feces sampling and detecting device, which overcomes the defects, like difficulty in moulding and poor safety, of the existing feces sampling and detecting device.

Another purpose of the present invention is to provide a method for detecting feces based on the feces sampling and detecting device of the present invention, which overcomes the defect of a long interval between collecting and detecting of the existing device.

On one hand, the present invention provides a feces sampling and detecting device; the device comprises a detector, detecting strips provided in the detector, a collector accommodated in the detector detachably, a feces sampler for sealing the collector detachably, and at least one puncturing part arranged at a bottom of the detector facing one side of the collector.

Furthermore, both the detector and the collector comprise a side wall and a bottom combined with the side wall, and both bottom area and height of the collector are less than that of the detector.

Furthermore, the sum of heights of the feces sampler combined with collector and height of the puncturing part is less than or equal to the height of the detector.

Furthermore, the shapes of the collector and the detector are same.

Furthermore, the bottom of the collector is made of a material which is easy to be punctured.

Furthermore, the bottom of the collector is made of aluminium foil.

Furthermore, there are two puncturing parts respectively arranged at two sides of a relatively long symmetry axis on a plane where the bottom of the detector and the bottom of the collector are superposed.

Furthermore, the puncturing part is cone-shaped, and a diameter of the puncturing part decreases gradually towards the collector from the bottom of the detector.

Furthermore, the puncturing part comprises multiple identical right triangles; a relatively short right-angle side of each right triangles clings to the bottom of the detector, and relatively long right-angle sides of each right triangle clings to each other, and a diameter of the puncturing part decreases gradually towards the collector from the bottom of the detector.

Furthermore, the feces sampler comprises a handle, a sampling rod and a sealing portion therebetween; the feces sampler is combined with the collector through the sealing portion, an end of the sampling rod which is far away from the handle is provided with screw threads extending from bottom to top.

Furthermore, the feces sampler comprises a handle and a sampling rod combined with the handle; an internal surface of the handle is provided with a sealing portion combined with the collector, an end of the sampling rod which is far away from the handle is provided with screw threads extending from bottom to top.

Furthermore, a membrane or a plug is provided in the collector, and a through hole for the sampling rod to pass through is provided at the centre of the membrane or the plug; the membrane or the plug divides a cavity of the collector into an observing cavity and a detecting cavity under the observing cavity; the length of the sampling rod is larger than the height of the observing cavity; the detecting cavity contains diluents; when the sampling rod passes through the through hole, the detecting cavity and the observing cavity are not communicated.

Furthermore, the through hole of the membrane extends downwards for 0.1-0.5 cm towards the bottom of the collector; the membrane is made of a compressible material; the diameter of the through hole is less than or equal to that of a part where the sampling rod and the through hole is combined, and the diameter of the through hole is equal to the external diameter of the screw thread.

Furthermore, the plug is made of a compressible material; the thickness of the plug is 0.5-2 cm.

Furthermore, the inside of the detector is provided with a detecting casse, the detecting casse clings to the side wall of the detector, and detecting strips are fixed in the detecting casse.

Furthermore, one surface of the detecting casse is provided with multiple grooves, and detecting strips are provided in the grooves.

Furthermore, two supporting bars extend from two ends at the bottom of the detecting casse; the sum of heights of the supporting bar and the groove is equal to the height of the detecting strip.

Furthermore, the detector is rectangle-shaped; at least one protuberant rib which is parallel to a side wall with a relatively large area is provided in the detector; a distance between the protuberant rib and the side wall with a relatively large area which is closest to the protuberant rib is equal to the thickness of a casse.

Furthermore, the collector, the handle and the sealing portion of the feces sampler coordinating with the collector are rectangle-shaped; a sealing ring is provided on the periphery of the sealing portion; and the sealing ring is rectangle-shaped.

Furthermore, the sealing portion of the feces sampler is cylinder-shaped; the sealing portion is provided with screw threads coordinating with the collector, and a corresponding tail end of screw threads of the collector is provided with a stop rotating part; the stop rotating part is a stop rotating slot or a stop rotating block.

Furthermore, a distance between two opposite side walls of the collector is less than or equal to a distance of the sealing portions coordinating with them.

Furthermore, the feces sampler is provided with protuberances along the periphery of the handle; a distance between the protuberances on the two opposite side of the handle is larger than a distance between the detecting casse which coordinate with the feces sampler and the opposite side of the detector.

Furthermore, the collector is made of a compressible material; a notch extending from top to bottom is provided at a top of a side wall of the detector.

Furthermore, the length of the notch is approximate to the height of the puncturing part, and the width of the notch is within ¼ to 1 of the width of a thumb.

Furthermore, the detector is a clear and colourless container made of a compressible material.

On the other hand, the present invention provides a method for detecting feces based on the feces sampling and detecting device, which comprises the following steps:

Step 1: sampling feces through a feces sampler;

Step 2: combining the feces sampler with sampled feces with a collector; and

Step 3: accommodating a device formed by combining the feces sampler with the collector in a detector; and puncturing the collector through a puncturing part in the detector, so that a feces sample flows into the detector, and then colour shows up on detecting strips of a detecting casse.

The present invention has the following beneficial effects: the feces sampling and detecting device of the present invention can detect the sampled feces quickly, thereby avoiding feces sample from changing in nature in an interval period.

The feces sampling and detecting device of the present invention has dual functions of collecting and detecting a feces sample, and a common operator can also detect without involving the medical staff.

In the feces sampling and detecting device of the present invention, a puncturing part is arranged at the bottom of the detector; the puncturing part adopts a design that the diameter of a cross section increases gradually from top to bottom, so when the collector gradually presses the puncturing part from top to bottom, the bottom of the collector can be punctured, and it is ensured that the diluents with the feces sample in the collector enter the detector to be detected.

The collector of the present invention is made of the compressible material, and the distance between the detecting casse of the detector and the side wall which is farthest from the casse is less than the distance between the protuberances of the handle of the feces sampler which coordinate with the casse and the side wall respectively. Thus, although the collector with the feces sampler is accommodated in the detector, the puncturing part of the detector still does not puncture the collector as long as the collector is not pressed, and unsafe usage of the device of the present invention will not be caused. So, the security of the device provided by the present invention is stilled guaranteed during transportation, sales and other unused states.

The collector of the present invention can be accommodated in the detector, and the feces sampler and the collector are coordinated together detachably; the design guarantees that the placing space is saved effectively before and after using the device of the present invention. Thus, the occupied space is reduced greatly during transportation and waste disposal.

The membrane of the collector of the present invention extends downwards along its through hole, the plug in the collector has a certain thickness, and the diameters of the through holes of the membrane and the plug are less than or equal to the diameter of the sampling rod; besides, the feces sampler coordinating with the collector is also provided with the sealing portion. Thus, the above double protections effectively prevents the dilutes in the collector from leaking outwards.

The notch with a certain width which extends downwards from the top is provided at a top of a side wall of the detector in the present invention; the notch is convenient for an operator to press, at the same time, it can also coordinate with an automatic detecting device to use.

DETAILED DESCRIPTION OF THE EMBODIMENTS

Embodiment 1

Figure 1:
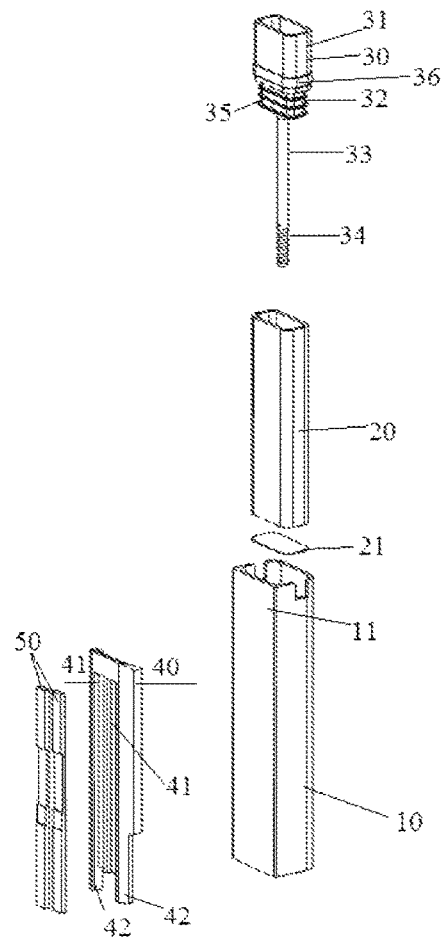
FIG. 1 shows an exploded view of a feces sampling and detecting device.

FIG. 1 shows an exploded view of the feces sampling and detecting device according to the present invention. The device comprises a detector 10, a collector 20 accommodated in the detector 10 detachably, a feces sampler 30 combined at the upper part in the collector 20 detachably, a detecting casse 40 provided in the detector 10 and detecting strips 50 fixed in the detecting casse 40.

The detector 10 is a cuboid-shaped one without a head cover; and the detector 10 is a clear and colourless container made of a compressible material.

The collector 20 in the detector 10 is also a cuboid-shaped one without a head cover; and the collector is made of a clear and colourless material. A lower surface of the collector 20 is sealed by aluminium foil 21. All of the length, width and height of the collector 20 are less than that of the detector 10 respectively, namely, both bottom area and height of the collector are less than that of the detector. Thus, the collector 20 can be completely accommodated in the detector 10.

The feces sampler 30 comprises a handle 31, a sealing portion 32 combined with a lower surface of the handle 31 and a sampling rod 33 which extends from a lower surface of the sealing portion 32 to a direction far away from the handle 31; an end of the sampling rod 33 which is far away from the handle 31 is provided with screw threads 34. The screw threads 34 extend upwards from a tail end of the sampling rod 33 to a position which is approximate to a third of the whole length of the sampling rod 33. The sum of heights of the sampling rod 33 and the sealing portion 32 is a little less than the height of the collector 20. The sum of heights of the handle 31 and the collector 20 is less than the height of the detector 10.

The handle 31 of the feces sampler 30 is a cuboid; both the length and width of the handle 31 are larger than that of the collector 20 respectively, and the length and width of the handle 31 are less than that of the detector 10 respectively. Thus, when the whole sampling rod 33 of the feces sampler 30 enters into the collector 20, the whole handle 31 buckles on the top of the collector 20, and the handle 31 is provided in the detector 10.

Both the length and width of the handle 31 of the feces sampler 30 are less than that of the detector 10 respectively. Thus, the feces sampler 30 combined with the collector 20 can move with the collector 20 in the detector 10.

A circle of protuberances 36 is provided on the periphery of the handle 31 along its cross section; a distance between the protuberances 36 provided on two opposite sides of the handle is larger than a distance between two sides of the handle.

The sealing portion 32 of the feces sampler 30 is a cuboid; both the length and width of the sealing portion 32 are less than that of the collector 20 respectively. Multiple sealing rings 35 are provided on the periphery of the sealing portion 32 of the cuboid; the distance between the sealing rings 35 which are provided on two opposite sides of the sealing portion is larger than or equal to the distance between two opposite sides of the collector 20 coordinating with the sealing rings 35. Thus, when the whole sampling rod 33 of the feces sampler 30 enters into the collector 20, the sealing ring 35 of the sealing portion 32 combines with the collector 20, so as to prevent the sample in the collector 20 from leaking from the collector 20, and prevent the feces sampler 30 from pulling away easily from the collector 20. The sealing portion 32 can also be designed as a sealing portion with sealing members, like a sealing snap joint.

The detecting casse 40 is approximate to a cuboid, which is just provided in the detector 10, and clings to the side wall 11 with a relatively large area. One side of the detecting casse 40 is provided with multiple grooves 41, and detecting strips 50 are provided in the grooves 41 of the detecting casse 40.

Two supporting bars 42 extend from two ends at the bottom of the detecting casse 40; the supporting bars 42 are used for standing the detecting casse 40 in the detector 10. The supporting bars are mainly convenient for a lower end of the detecting strip in the detecting casse 40 to directly contact the diluents, which is convenient for the diluents upwards extending along the detecting strip.

The sum of heights of the supporting bar 42 and the groove 41 is equal to the height of the detecting strip 50. Thus, when the detecting strips are in the detector 10, the bottom of the detecting strips contact the bottom surface of the detector 10.

Figure 2:
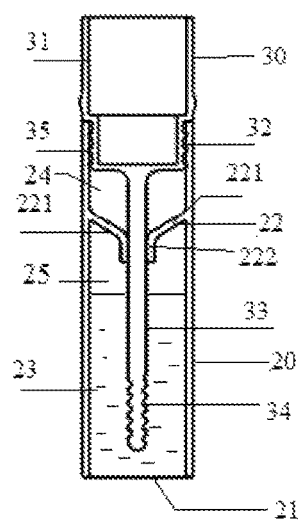
FIG. 2 shows a section view of combination between a feces sampler and a collector.

FIG. 2 shows a section view of combination between a feces sampler 30 and a collector 20. In the section view, the sampling rod 33 of the feces sampler 30 enters into the collector 20.

A membrane 22 is provided in the cavity of the collector 20; the membrane 22 is made of an elastic compressible material, including silica gel and so on. The height of the cavity formed by the membrane 22 and the top of the collector 20 is larger than that of the sealing portion 32 of the feces sampler 30. Thus, the membrane 22 divides the cavity of the collector 20 into an upper observing cavity 24 and a lower detecting cavity 25; the length of the sampling rod 33 is larger than the height of the observing cavity 24.

A specified volume of diluents 23 is provided in the detecting cavity below the membrane 22 of the collector 20; the diluents can be either pure water or other liquid.

The membranes 22 are arranged along the cross section of the cavity of the collector 20, including four separating membranes 221 which extend from inner walls of four sides of the cavity of the collector 20 to a centre; each separating membrane 221 inclines downwards relative to the horizontal plane; the four separating membranes 221 gather together to form a through hole 222 at the centre. The diameter of the through hole 222 is less than or equal to that of a part where the sampling rod and the through hole is combined, so the sampling rod 33 and the through hole 222 form an interference fit. Besides, the diameter of the through hole 222 is equal to an external diameter of the screw threads 34 of the sampling rod 33.

When the sampling rod 33 with sampled feces enters into the diluents 23 of the collector through the through hole 222, the feces gathering in the screw threads 34 of the sampling rod 33 are dissolved completely in the specified volume of diluents 23. In addition, because the diameter of the through hole 222 is equal to the external diameter of the screw threads of the sampling rod 33, the volume of all feces which can be accommodated in the screw threads can be calculated, so that a concentration of the feces in the diluents is calculated.

The through hole 222 of the membrane extends towards the bottom of the collector 20 for about 0.1-0.5 cm, thereby the whole through hole 222 wraps the periphery of the sampling rod 33 when the sampling rod 33 passes through the through hole 222, which plays a role in sealing and effectively prevents the diluents with the sample in the collector 20 from leaking.

Similarly, because the diameter of the through hole 222 is equal to the external diameter of the screw threads of the sampling rod 33, and there is a gap between the sealing portion 32 of the feces sampler 30 and the membrane 22, when redundant feces sampled by the sampling rod 33 is left on the membrane 22, the medical staff can observe the colour and state of the redundant feces through a transparent outer wall of the collector 20, so as to diagnose whether the person detected suffers from disease of digestive tract.

The sealing ring 35 of the sealing portion 32 of the feces sampler 30 is combined with the upper part of the cavity of the collector 20, so the double protection of the through hole 222 and the sealing ring 35 effectively prevents the diluents 23 from leaking from the collector 20. Even the collector 20 is transported for a long distance, the sample in the collector 20 hardly leaks therefrom.

The handle 31 of the feces sampler 30 is provided above the collector 20, and the bottom of the handle 31 is combined with a top wall of the collector 20.

The bottom of the collector 20 is sealed by the aluminium foil 21; the aluminium foil 21 can also be replaced by other thinner material which is easy to be punctured.

The above feces sampler 30 and the collector 20 can be combined into one, so as to be used coordinating with a detecting machine as a separate feces sampling device; or, they are used coordinating with the detecting device under the operation of a specialized operator.

Figure 3:
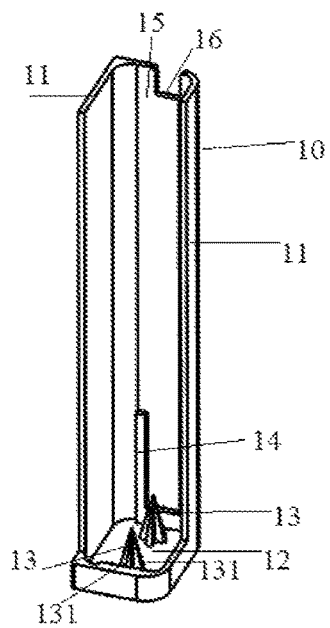
FIG. 3 shows a partial section view of a detector.

FIG. 3 shows a partial section view of the detector 10. Puncturing parts 13 are provided on the bottom 12 of the detector 10, wherein the bottom faces towards the cavity of the detector. There are two puncturing parts 13 in the embodiment 1, which are respectively arranged at two sides of the relatively long symmetry axis on the plane where the bottom of the detector 10 and the bottom of the collector are superposed. The puncturing part 13 is generally cone-shaped, and a diameter of the puncturing part 13 decreases gradually towards the collector 20 from the bottom of the detector. Optionally, the puncturing part 13 may comprises multiple identical right triangles 131, a relatively short right-angle side of each of the right triangles 131 clings to the bottom 12 of the detector 10, and relatively long right-angle side of each of the right triangles 131 clings to each other to form the puncturing part 13 whose diameter increases gradually from top to bottom. The sum of the heights of the combined feces sampler 30 and the collector 20 and the height of the puncturing part 13 is less than or equal to the height of the detector 10, thereby ensuring that the feces sampling and detecting device is still a whole after the detection is finished, which is convenient for abandoning.

The protuberant ribs 14 which are parallel to the side wall 11 with a relatively large area are provided in the cavity of the detector 10; there are two protuberant ribs 14 which are provided at two sides of the symmetry axis of the detector 10. The protuberant ribs 14 extend upwards from the bottom of the detector 10 to a ¼-⅓ position of the height of the detector 10. The distance between the protuberant ribs 14 and the side wall 11 with a relatively large area is equal to the thickness of the casse 40, so the space between the protuberant ribs 14 and the side wall with a relatively large area is used for accommodating the detecting casse 40.

A notch 16 is provided at a top of a side wall 15 with a relatively small area of the detector 10; the width of the notch 16 is ¼-1 of the width of a thumb, and the length of the notch is approximate to the height of the puncturing part. The notch 16 is used for the operator to place a finger when pressing the collector 20 in the detector 10. In addition, the notch 16 can also be used coordinating with the automatic detecting device, it is convenient for the detecting device to press the sampler 30 and the collector 20 to make the puncturing part 13 puncture the aluminium foil 21, and then the diluents with the feces sample outflows to detect.

Figure 4:
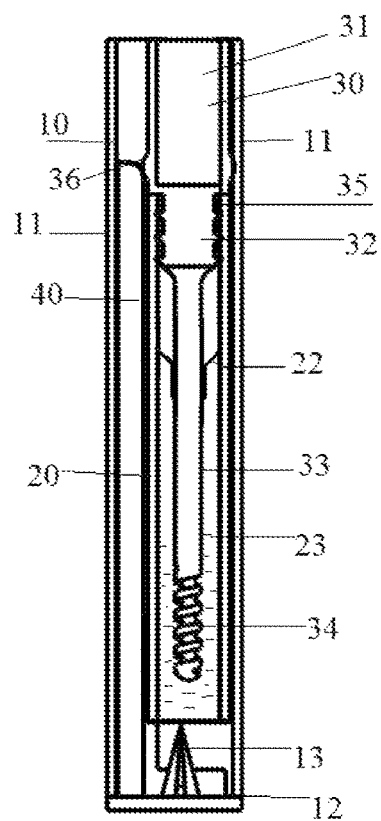
FIG. 4 shows a first state view in use of the feces sampling and detecting device according to the present invention.

FIG. 4 shows the feces sampling and detecting device of the present invention; in the device, the feces sampler 30 is provided in the collector 20, and they are provided in the detector 10 with the casse 40 together. The sum of the thickness of the casse 40 and the width of the collector 20 is a little less than the width of the detector 30. The width of the handle 31 of the feces sampler 30 is equal to that of the collector 20. An arc-shaped protuberance can be provided on one side of the casse 40 facing towards the collector 20; when the puncturing part 13 punctures the aluminium foil 21 at the bottom of the collector 20, and the collector 20 moves downwards, the arc-shaped protuberance extrudes the collector 20, which is convenient for the liquid in the collector 20 to outflow from the hole formed by puncturing the aluminium foil 21.

The sum of the height of the puncturing part 13 arranged on the bottom 12 of the detector 40 and the height of the collector 20 and the height of the handle 31 of the feces sampler 30 exposed out of the collector 20 is equal to the height of the detecting device, or the sum of the height of the puncturing part 13 arranged on the bottom 12 of the detector 40 and the height of the collector 20 and the height of the handle 31 of the feces sampler 30 exposed out of the collector 20 is less than the height of the detecting device.

In addition, the distance between two protuberances 36 on two opposite sides of the handle 31 is larger than the distance between the casse 40 and the side wall 11 with a relatively large area of the detector which is opposite to the casse. At the point, the protuberance 36 of the handle 31 of the feces sampler 30 is just on the top of the casse 40, so the casse 40 just supports the whole collector and the feces sampler 30 when the handle 31 of the feces sampler 30 is not pressed, so as to prevent the collector 20 from falling free because of gravity to be punctured by the puncturing part 13; so the security of the device provided by the present invention is still guaranteed during transportation, sales and other unused states.

Figure 5:
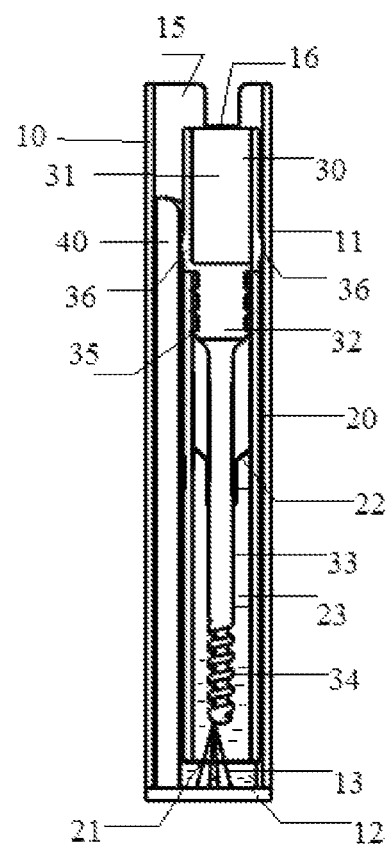
FIG. 5 shows a second state view in use of the feces sampling and detecting device according to the present invention.

FIG. 5 shows a second state view in use of the feces sampling and detecting device according to the present invention. In the state, the operator presses the handle 31 of the feces sampler 30 through the notch 16 of the detector 10; by pressing, the protuberances 36 of the handle 31 can move downwards through the casse 40. When the bottom 21 of the collector 20 contacts the puncturing part 13, the operator continues to press the handle 31, and then the puncturing part 13 punctures the bottom 21 of the collector 20 more, so the liquid sample in the collector 20 outflows from the collector 20. The liquid sample flows into the detector 10, and then the liquid sample in the detector 10 climbs up along the detecting strip 50 in the casse 40; when the liquid sample contains substances to be detected, and the concentration of the substances to be detected reaches a detecting critical value of the detecting strip, colour shows up on the detecting strip. Thus, the medical staff can directly detect whether the person detected suffers from disease of digestive tract.

After the detection is finished, the medical staff do not need to take the collector 20 out, but can directly abandon it according to the state in FIG. 5. The tight combination at the contact of the protuberance 36 of the handle 31 and the casse 40 can effectively prevent the diluents with dissolved sample to be detected from leaking from the detector 10, thereby preventing environment pollution.

Embodiment 2

Figure 6:
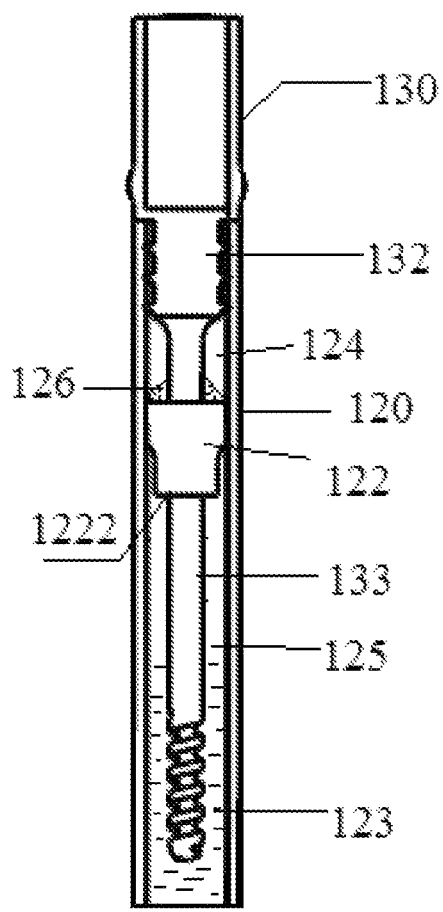
FIG. 6 shows a perspective view of combination between the feces sampler and the collector according to an embodiment 2 of the present invention.

FIG. 6 shows a perspective view of combination of a feces sampler 130 and a collector 120; the collector 120 in the present embodiment is different from the collector 20 in the embodiment 1, and the feces sampler 130 in the present embodiment is the same as the feces sampler 30 in the embodiment 1.

The difference between the collector 120 in the present embodiment and the collector 20 in the embodiment 1 is that the membrane 22 is replaced by a plug 122 in the present embodiment. The plug is also made of the compressible material as the membrane, including silica gel and so on. In the present embodiment, the plug 122 is combined to the whole side wall of the collector 120 to form a plug of the collector with a certain thickness; for example, the thickness of the plug is within 0.5-2 cm. A through hole 1222 which passes through the whole plug 122 is provided at the symmetry centre of the plug 122; the diameter of the through hole 1222 is less than or equal to that of the sampling rod 33 of the feces sampler. Because the plug 122 has a certain thickness, when the sampling rod passes through the plug 122, the plug 122 plays a certain role in sealing. The cavity of the collector 120 is divided into an upper observing cavity 124 and a lower detecting cavity 125 by the plug 122; when the feces sampler 130 is combined with the collector 120, the two cavities are disconnected, and diluents 123 and the feces sample dissolved in the diluents 123 can not leak into the observing cavity 124.

When the feces sampler 130 is combined to the collector 120, a certain gap is formed between the upper surface of the plug 122 and a sealing portion 132 of the feces sampler 130. Thus, when redundant feces 126 sampled by the sampling rod 133 is left on the upper surface of the plug 122, the medical staff can observe the colour and state of the redundant feces through the observing cavity 124 of the collector 120, so as to diagnose whether the person detected suffers from disease of digestive tract.

The settings of other parts of the collector 120 in the present embodiment are the same as that in the embodiment 1.

Embodiment 3

Figure 7:
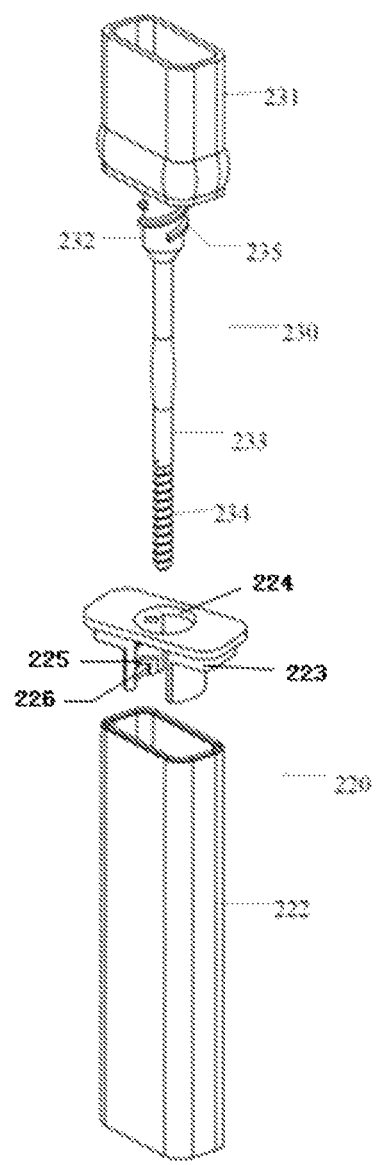
FIG. 7 shows an exploded view of the feces sampler and the collector according to an embodiment 3 of the present invention.

FIG. 7 shows an exploded view of a feces sampler 230 and a collector 220 of the present invention.

The feces sampler 230 comprises a handle 231, a sealing portion 232 combined with the lower surface of the handle 231 and a sampling rod 233 which extends from the sealing portion 232 to a direction far away from the handle 231. The end of the sampling rod 233 which is far away from the handle 231 is arranged with screw threads 234. The screw threads 234 extend upwards from the tail end of the sampling rod 233 to a ⅓ position of the whole length of the sampling rod.

There are screw threads 235 provided on the periphery of the sealing portion 232.

The collector 220 comprises a cavity 222 and a head cover 223 combined to the top of the cavity 222; there is an opening 224 provided at the head cover 223; there are internal screw threads 225 coordinating with the external screw threads 235 of the sealing portion 232 provided in the opening 224; a stop rotating block 226 is provided at the tail end of the screw threads of the opening 224.

Figure 8:
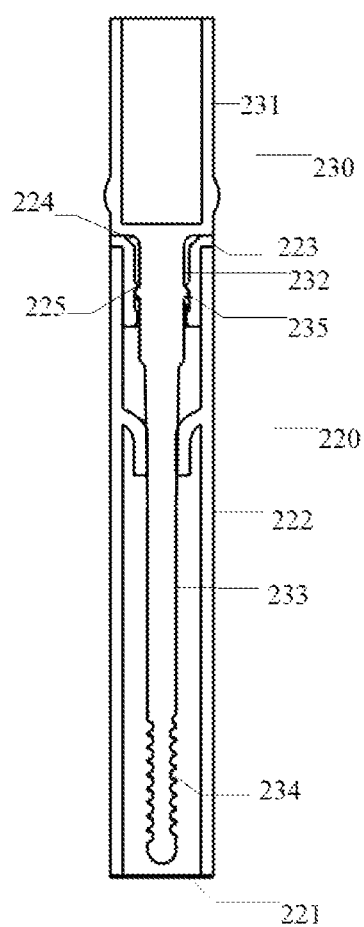
FIG. 8 shows a section view of combination between the feces sampler and the collector according to the embodiment 3 of the present invention.

FIG. 8 shows a section view of combination of the feces sampler 230 and the collector 220. The head cover 223 is provided at the top of the cavity 222; there are internal screw threads 225 provided in the opening 224; the internal screw threads are combined with the external screw threads 235 of the sealing portion 232, thereby preventing the sample in the collector 220 from leaking.

The detector 210, the casse 240 and the detecting strip 250 in the present embodiment are the same as that in the embodiment 1.

The coordination relationship between the collector and the detector in the present embodiment is also the same as that in the embodiment 1.

Embodiment 4

Figure 9:
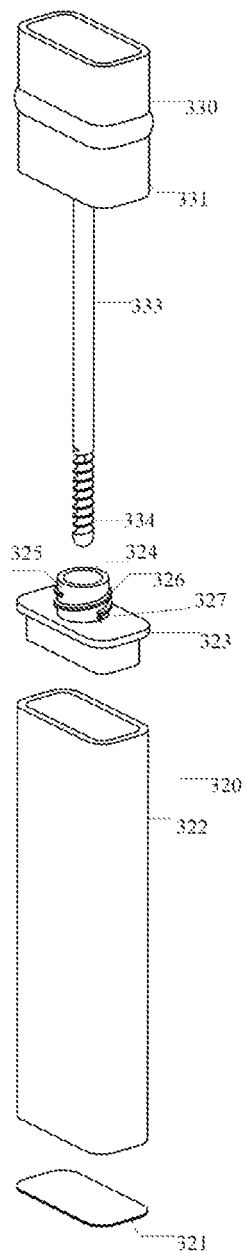
FIG. 9 shows an exploded view of the feces sampler and the collector according to an embodiment 4 of the present invention.

FIG. 9 shows an exploded view of a feces sampler 330 and a collector 320 of the present invention.

The feces sampler 330 comprises a handle 331 and a sampling rod 333 which extends from the lower part of the handle 331 to a direction far away from the handle 331. The end of the sampling rod 333 which is far away from the handle 331 is arranged with screw threads 334. The screw threads 334 extend upwards from the tail end of the sampling rod 333 to a ⅓ position of the whole length of the sampling rod.

The collector 320 comprises a cavity 322, aluminium foil 321 combined to the bottom of the cavity 322 and a head cover 323 combined to the top of the cavity 322. The aluminium foil 321 combined to the bottom of the cavity can be replaced by other material which is moulded with the cavity 322 integrally and the thickness of which is smaller than that of the cavity. A cylinder-shaped tube 325 extends from the head cover 323 towards the handle 331; a circular opening 324 is provided at the top of the cylinder-shaped tube 325; external screw threads 326 matching with the internal screw threads of the handle are provided on an outer surface of the cylinder-shaped tube 325; the tail end of the external screw thread 326 which is close to the head cover is provided with a stop rotating part; the stop rotating part in the present embodiment is stop rotating block 327, thereby preventing too tight screwing while screwing the screw threads.

Figure 10:
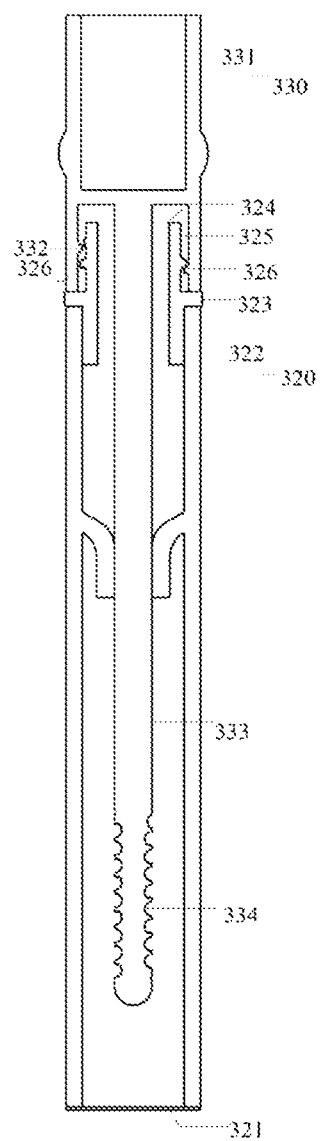
FIG. 10 shows a section view of combination between the feces sampler and the collector according to the embodiment 4 of the present invention.

FIG. 10 shows a section view of combination between the feces sampler 330 and the collector 320.

It can be seen from the section view that internal screw threads 332 are provided on an inner surface of the handle 331; the internal screw threads 332 are combined with the external screw threads 326 of the cylinder-shaped tube 325 of the head cover 323, which makes it difficult for the sample in the collector to leak from the collector.

The detector 310, the casse 340 and the detecting strip 350 in the present embodiment are the same as that in the embodiment 1.

The coordination relationship between the collector and the detector in the present embodiment is also the same as that in the embodiment 1.

Finally, to be clear, the above embodiments are only used for illustrating the technical solutions of the present invention and not intended to limit the technical solutions; the present invention can be extended to other modifications, changes, applications and embodiments on the application, therefore it is considered that all the modifications, changes, applications and embodiments shall fall within the spirit and scope of the present invention.

The invention claimed is:

1. A feces sampling and detecting device comprising:
a detector, wherein a plurality of detecting strips are provided in the detector;
a collector accommodated in the detector detachably;
a feces sampler for sealing the collector detachably; and
at least one puncturing part arranged at a bottom of the detector and facing the collector,
wherein the feces sampling and detecting device further comprises a notch provided at a top of a sidewall of the detector, the sidewall having a top and an opposite bottom, the notch extending downwardly from the top of the sidewall;
wherein the notch has a length extending downwardly from the top of the sidewall and the puncturing part has a height extending upwardly from the bottom of the detector, the length being substantially equal to the height;
wherein the notch has a width substantially perpendicular to the length, the width being adapted to allow a user to place a finger for pressing the collector or allow an automatic machine to press the collector to puncture the collector by the puncturing part; and
wherein the sum of the combined height of the feces sampler and the collector and the height of the puncturing part is less than or equal to the height of the detector, such that the top surface of the collector is below or in flush with the top surface of the detector prior to the puncturing of the collector by the puncturing part,
wherein:
the puncturing part comprises a plurality of identical right triangles attached to one another;
relatively long right-angle sides of the plurality of identical right triangles are attached to one another to form a central post, such that the plurality of identical right triangles are attached to one another through the central post, wherein the plurality of identical right triangles are disposed radially equaldistantly with respect to the central post;
a relatively short right-angle side of each of the right triangles is attached to the bottom of the detector; and
a diameter of the puncturing part decreases gradually towards the collector from the bottom of the detector.

2. The device according to claim 1, wherein both the detector and the collector comprise a side wall and a bottom combined with the side wall, and both bottom area and height of the collector are less than that of the detector.

3. The device according to claim 2, wherein the bottom of the collector is made of aluminium foil.

4. The device according to claim 1 or 2,
wherein there are two puncturing parts which are respectively arranged at two sides of a relatively long symmetry axis on a plane where the bottom of the detector and the bottom of the collector are superposed.

5. The device according to claim 1, wherein the feces sampler comprises a handle, a sampling rod and a sealing portion between the handle and the sampling rod; the feces sampler is combined with the collector through the sealing portion; an end of the sampling rod which is far away from the handle is provided with screw threads extending from bottom to top.

6. The device according to claim 1, wherein the feces sampler comprises a handle and a sampling rod which is combined with the handle; an internal surface of the handle is provided with a sealing portion which is combined with the collector; an end of the sampling rod which is far away from the handle is provided with screw threads extending from bottom to top.

7. The device according to claim 5 or 6, wherein a membrane or a plug is provided in the collector, and a through hole for the sampling rod to pass through is provided at the centre of the membrane or the plug; the membrane or the plug divides a cavity of the collector into an observing cavity and a detecting cavity under the observing cavity; the length of the sampling rod is larger than the height of the observing cavity; the detecting cavity contains diluents; when the sampling rod passes through the through hole, the detecting cavity and the observing cavity are disconnected.

8. The device according to claim 7, wherein the through hole of the membrane extends downwards for 0.1-0.5 cm towards the bottom of the collector; the membrane is made of a compressible material; the diameter of the through hole is less than or equal to that of a part where the sampling rod and the through hole is combined, and the diameter of the through hole is equal to the external diameter of the screw thread.

9. The device according to claim 7, wherein the plug is made of a compressible material; the thickness of the plug is within 0.5-2 cm.

10. The device according to claim 2, wherein the inside of the detector is provided with a detecting casse, the detecting casse clings to the side wall of the detector, and detecting strips are fixed in the detecting casse.

11. The device according to claim 10, wherein one surface of the detecting casse is provided with multiple grooves, and detecting strips are provided in the grooves.

12. The device according to claim 11, wherein two supporting bars extend from two ends at the bottom of the detecting casse; the sum of heights of the supporting bar and the groove is equal to the height of the detecting strip.

13. The device according to claim 10, wherein the detector is rectangle-shaped; at least one protuberant rib which is parallel to a side wall with a relatively large area is provided in the detector; a distance between the protuberant rib and the side wall with a relatively large area which is closest to the protuberant rib is equal to the thickness of a casse.

14. The device according to claim 5 or 6, wherein the collector, the handle and the sealing portion of the feces sampler coordinating with the collector are rectangle-shaped; and a sealing ring which is rectangle-shaped is provided on the periphery of the sealing portion.

15. The device according to claim 6, wherein the sealing portion of the feces sampler is cylinder-shaped; the sealing portion is provided with screw threads coordinating with the collector, and a corresponding tail end of screw threads of the collector is provided with a stop rotating part; the stop rotating part is a stop rotating slot or a stop rotating block.

16. The device according to claim 14, wherein a distance between two opposite side walls of the collector is less than or equal to a distance of the sealing portions coordinating with them.

17. The device according to claim 10, wherein the feces sampler is provided with protuberances along the periphery of the handle; a distance between the protuberances on the two opposite side of the handle is larger than a distance between the detecting casse which coordinate with the feces sampler and the opposite side of the detector.

18. The device according to claim 1, wherein the collector is made of a compressible material; and the width of the notch is within ¼ to 1 of the width of a thumb of the user.

19. The device according to claim 1, wherein the detector is a clear and colourless container made of a compressible material.

20. A method for detecting feces based on the feces sampling and detecting device according to claim 1, comprising:

Step 1: sampling feces through the feces sampler;
Step 2: combining the feces sampler with sampled feces with the collector, and
Step 3: accommodating a device formed by combining the feces sampler with the collector in the detector, and puncturing the collector through the puncturing part in the detector by pressing the collector through the notch, so that a feces sample flows into the detector, and then colour shows up on detecting strips of a detecting casse.

\* \* \* \* \*